(12) United States Patent
Kramer et al.

(10) Patent No.: US 7,232,796 B2
(45) Date of Patent: Jun. 19, 2007

(54) MEDICAMENT CONTAINING A TISSUE INHIBITOR OF METALLOPROTEINASES-2 (TIMP-2) AS AN OSTEOANABOLICALLY ACTIVE SUBSTANCE

(75) Inventors: Franz-Josef Kramer, Springe (DE); Silke Mark, Felsberg-Gensungen (DE); Ludger Ständker, Hannover (DE); Wolf-Georg Forssmann, Hannover (DE)

(73) Assignee: IPF PharmaCeuticals GmbH, Hannover (DE)

( * ) Notice: Subject to any disclaimer, the term of this patent is extended or adjusted under 35 U.S.C. 154(b) by 0 days.

(21) Appl. No.: 10/239,870

(22) PCT Filed: Apr. 4, 2001

(86) PCT No.: PCT/EP01/04891

§ 371 (c)(1),
(2), (4) Date: Dec. 11, 2002

(87) PCT Pub. No.: WO01/74380

PCT Pub. Date: Oct. 11, 2001

(65) Prior Publication Data

US 2003/0195143 A1    Oct. 16, 2003

(30) Foreign Application Priority Data

Apr. 5, 2000    (DE) .................. 100 16 791

(51) Int. Cl.
*A61K 38/00*    (2006.01)
*A61K 49/00*    (2006.01)

(52) U.S. Cl. ................... 514/2; 514/12; 530/350; 530/344; 530/345; 435/7.1; 424/9.1

(58) Field of Classification Search .............. 514/12, 514/2; 530/350, 344, 345; 435/7.1, 23; 424/9.1

See application file for complete search history.

(56) References Cited

U.S. PATENT DOCUMENTS

| | | | |
|---|---|---|---|
| 5,595,885 A | 1/1997 | Stetler-Stevenson et al. |
| 5,643,752 A | 7/1997 | Hawkins et al. |
| 5,714,465 A | 2/1998 | Langley et al. |
| 5,766,585 A | 6/1998 | Evans et al. |

FOREIGN PATENT DOCUMENTS

| EP | 623676 A1 * 11/1994 |
|---|---|
| WO | WO 98/04287    5/1998 |

OTHER PUBLICATIONS

Voet et al., Biochemistry (John Wiley & Sons published), pp. 62-63 (1990).*
Guo et al., PNAS 101,9205-9210 (2004).*
Yamashita et al., "*Tyrosine phosphorylation is crucial for grown signaling by tissue inhibitors of metalloproteinases(TIMP-1 and TIMP-2)*", *FEBS Letters*, vol. 396, 103-107 (1996).

* cited by examiner

*Primary Examiner*—Chih-Min Kam
(74) *Attorney, Agent, or Firm*—Jacobson Holman PLLC

(57) ABSTRACT

The invention relates to tissue inhibitor of metalloproteinase-2 (TIMP-2) as an osteoanabolically active peptide for use as a medicament for treating bone defects, bone diseases and for improving bone regeneration.

3 Claims, 2 Drawing Sheets

A

B

SEQUENCE LISTING

```
<160> NUMBER OF SEQ ID NOS: 4

<210> SEQ ID NO 1
<211> LENGTH: 194
<212> TYPE: PRT
<213> ORGANISM: Homo sapiens

<400> SEQUENCE: 1

Cys Ser Cys Ser Pro Val His Pro Gln Gln Ala Phe Cys Asn Ala Asp
1               5                   10                  15

Val Val Ile Arg Ala Lys Ala Val Ser Glu Lys Glu Val Asp Ser Gly
            20                  25                  30

Asn Asp Ile Tyr Gly Asn Pro Ile Lys Arg Ile Gln Tyr Glu Ile Lys
        35                  40                  45

Gln Ile Lys Met Phe Lys Gly Pro Glu Lys Asp Ile Glu Phe Ile Tyr
    50                  55                  60

Thr Ala Pro Ser Ser Ala Val Cys Gly Val Ser Leu Asp Val Gly Gly
65                  70                  75                  80

Lys Lys Glu Tyr Leu Ile Ala Gly Lys Ala Glu Gly Asp Gly Lys Met
                85                  90                  95
```

His Ile Thr Leu Cys Asp Phe Ile Val Pro Trp Asp Thr Leu Ser Thr
            100                 105                 110

Thr Gln Lys Lys Ser Leu Asn His Arg Tyr Gln Met Gly Cys Glu Cys
        115                 120                 125

Lys Ile Thr Arg Cys Pro Met Ile Pro Cys Tyr Ile Ser Ser Pro Asp
    130                 135                 140

Glu Cys Leu Trp Met Asp Trp Val Thr Glu Lys Asn Ile Asn Gly His
145                 150                 155                 160

Gln Ala Lys Phe Phe Ala Cys Ile Lys Arg Ser Asp Gly Ser Cys Ala
            165                 170                 175

Trp Tyr Arg Gly Ala Ala Pro Pro Lys Gln Glu Phe Leu Asp Ile Glu
            180                 185                 190

Asp Pro

<210> SEQ ID NO 2
<211> LENGTH: 162
<212> TYPE: PRT
<213> ORGANISM: Homo sapiens

<400> SEQUENCE: 2

Cys Ser Cys Ser Pro Val His Pro Gln Gln Ala Phe Cys Asn Ala Asp
1               5                   10                  15

Asn Asp Ile Tyr Gly Asn Pro Ile Lys Arg Ile Gln Tyr Glu Ile Lys
            20                  25                  30

Thr Ala Pro Ser Ser Ala Val Cys Gly Val Ser Leu Asp Val Gly Gly
        35                  40                  45

Lys Lys Glu Tyr Leu Ile Ala Gly Lys Ala Glu Gly Asp Gly Lys Met
    50                  55                  60

His Ile Thr Leu Cys Asp Phe Ile Val Pro Trp Asp Thr Leu Ser Ile
65                  70                  75                  80

Thr Gln Lys Lys Ser Leu Asn His Arg Tyr Gln Met Gly Cys Glu Cys
            85                  90                  95

Lys Ile Thr Arg Cys Pro Met Ile Pro Cys Tyr Ile Ser Ser Pro Asp
            100                 105                 110

Glu Cys Leu Trp Met Asp Trp Val Thr Glu Lys Ser Ile Asn Gly His
            115                 120                 125

Gln Ala Lys Phe Phe Ala Cys Ile Lys Arg Ser Asp Gly Ser Cys Ala
        130                 135                 140

Trp Tyr Arg Gly Ala Ala Pro Pro Lys Gln Glu Phe Leu Asp Ile Glu
145                 150                 155                 160

Asp Pro

<210> SEQ ID NO 3
<211> LENGTH: 194
<212> TYPE: PRT
<213> ORGANISM: Artificial
<220> FEATURE:
<223> OTHER INFORMATION: Consesus sequence for TIMP-2
<220> FEATURE:
<221> NAME/KEY: MISC_FEATURE
<222> LOCATION: (57)..(57)
<223> OTHER INFORMATION: Glu or Asp
<220> FEATURE:
<221> NAME/KEY: MISC_FEATURE
<222> LOCATION: (111)..(111)
<223> OTHER INFORMATION: Thr or Ile
<220> FEATURE:
<221> NAME/KEY: MISC_FEATURE
<222> LOCATION: (156)..(156)

-continued

<223> OTHER INFORMATION: Asn or Ser

<400> SEQUENCE: 3

Cys Ser Cys Ser Pro Val His Pro Gln Gln Ala Phe Cys Asn Ala Asp
1               5                   10                  15

Val Val Ile Arg Ala Lys Ala Val Ser Glu Lys Glu Val Asp Ser Gly
            20                  25                  30

Asn Asp Ile Tyr Gly Asn Pro Ile Lys Arg Ile Gln Tyr Glu Ile Lys
        35                  40                  45

Gln Ile Lys Met Phe Lys Gly Pro Xaa Lys Asp Ile Glu Phe Ile Tyr
    50                  55                  60

Thr Ala Pro Ser Ser Ala Val Cys Gly Val Ser Leu Asp Val Gly Gly
65                  70                  75                  80

Lys Lys Glu Tyr Leu Ile Ala Gly Lys Ala Glu Gly Asp Gly Lys Met
                85                  90                  95

His Ile Thr Leu Cys Asp Phe Ile Val Pro Trp Asp Thr Leu Xaa Thr
            100                 105                 110

Thr Gln Lys Lys Ser Leu Asn His Arg Tyr Gln Met Gly Cys Glu Cys
            115                 120                 125

Lys Ile Thr Arg Cys Pro Met Ile Pro Cys Tyr Ile Ser Ser Pro Asp
130                 135                 140

Glu Cys Leu Trp Met Asp Trp Val Thr Glu Lys Xaa Ile Asn Gly His
145                 150                 155                 160

Gln Ala Lys Phe Phe Ala Cys Ile Lys Arg Ser Asp Gly Ser Cys Ala
                165                 170                 175

Trp Tyr Arg Gly Ala Ala Pro Pro Lys Gln Glu Phe Leu Asp Ile Glu
            180                 185                 190

Asp Pro

<210> SEQ ID NO 4
<211> LENGTH: 24
<212> TYPE: PRT
<213> ORGANISM: Rattus rattus
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 4

Xaa Ser Xaa Ser Pro Val His Pro Gln Gln Ala Phe Xaa Asn Ala Asp
1               5                   10                  15

Val Val Ile Arg Ala Lys Ala Val
            20

MEDICAMENT CONTAINING A TISSUE INHIBITOR OF METALLOPROTEINASES-2 (TIMP-2) AS AN OSTEOANABOLICALLY ACTIVE SUBSTANCE

This application is a 371 of PCT/EP01/04891, filed Apr. 4, 2001.

This is a nationalization of PCT/EP01/04891, filed Apr. 4, 2001 and published in German.

The invention relates to a medicament and a diagnostic agent containing tissue inhibitor of metalloproteinases-2 (TIMP-2) as an osteoanabolically active peptide preparation, and the use thereof.

TIMP-2 belongs to the family of "tissue inhibitors of metalloproteinases", of which four different peptides (TIMP-1 to TIMP-4) having different biological functions have been known to date.

The primary structure of TIMP-2 could be elucidated for various organisms, such as humans (Liotta et al., 1991), rats (Roswit et al., 1992), and mice (Kishi et al., 1991). The peptide contains a total of 12 cysteines which are linked to one another through 6 cystine bridges.

The biological functions of TIMP-2 include, inter alia, the inhibition of active matrix metalloproteinases (MMPs). The term MMPs refers to a group of zinc-dependent endoproteinases which are capable of degrading the extracellular matrix. The extracellular matrix consists of a complex structure and is constituted, inter alia, of collagen, proteoglycans, glycoproteins and glycosaminoglycans. Degradation of the extracellular matrix is essential to many biological processes, such as embryo-genesis, morphogenesis and tissue absorption and remodelling. However, uncontrolled activity of the MMPs can result in a considerable destruction of tissues, such as in rheumatic arthritis (Okada et al., 1986).

Further biological functions of TIMP-2 are related to the inhibition of the matrix metalloproteinases, including, inter alia, reduction of the growth of tumor cells (Gomez et al., 1997), and inhibition of angiogenesis (Valente et al., 1998).

In addition to these functions, intrinsic biological activities of TIMP-2 have also been described. These include an increased formation of red blood cells (Stetler-Stevenson et al., 1992), and a mitogenic effect on different cell lines (Hayakawa et al., 1994). Further, both inhibition of bone absorption in whole bone cultures (Hill et al., 1993) and stimulation of bone absorption by osteoclasts (Shibutani et al., 1999) could be shown in vitro.

Figure 1:
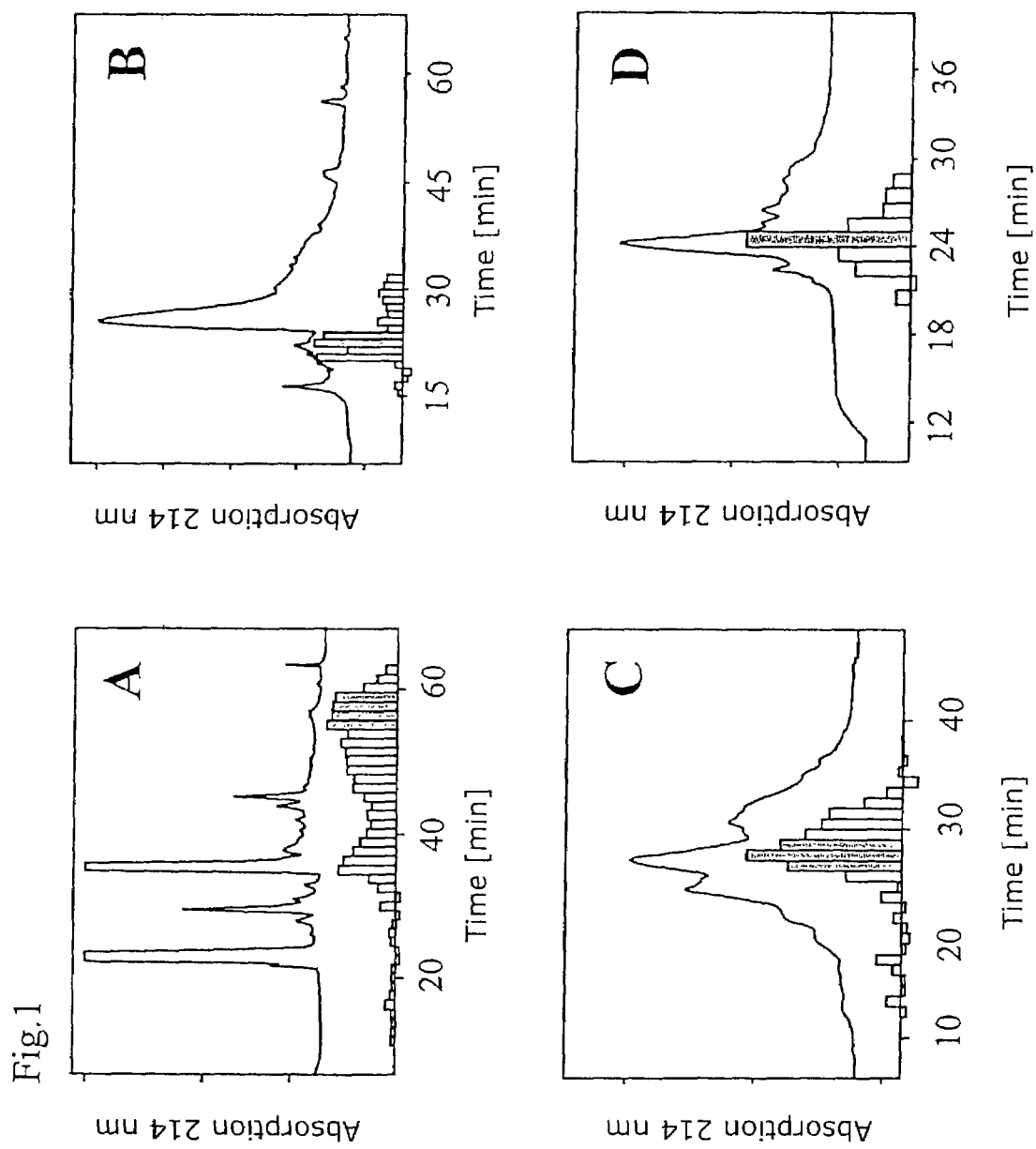
FIGS. 1A–1D show different chromatographic steps for the purification of osteoproliferative TIMP-2.

Surprisingly, TIMP-2 having the amino acid sequence $Z^1$CSCSPVHPQQAFCNADVVIRAKAVSEKEVDSGNDIYGNPIKRIQYEIKQIMFKGP(residues 1–56     ($Z^1$-SEQ ID NO: 3-$Z^2$)

of SEQ NO: 1)X1KDTEFIYTAPSSAVCGVSLDVGGKKEYLIAGKAEGDGKMHITLCDFIVPWDTL (residues 58–110 of SEQ ID NO: 1)X2TTQKKSLNHRYQMGCECKITRCPMIPCYISSPDECLWMDWV TEK(residues 112–155 of SEQ ID NO: 1)X3INGHQAKFFACIKRSDGSCAWYRGAAPPKQEFLDIEDP (residues 157–194 of SEQ ID NO: 1)-$Z^2$ wherein  X1 represents  the amino acid E or D;
              X2 represents  the amino acid T or I;
              X3 represents  the amino acid N or S;
              $Z^1$ represents  —H, a substituted group or an arbitrary peptide having up to ten amino acids;
              $Z^2$ represents  —OH, $NH_2$, a substituted —$NH_2$ or an arbitrary peptide having up to ten amino acids;

and its biologically active fragments and/or amidated, acylated, sulfated, phosphorylated, glycosylated and/or polyethylene-glycol modified derivatives, are capable of causing stimulation of the osteoblasts responsible for osteogenesis. TIMP-2 has a proliferative and protective effect on fetal osteoblasts.

Therefore, according to the invention, a medicament is claimed containing TIMP-2 having the amino acid sequence ($Z^1$-SEQ ID NO: 3-$Z^2$)
$Z^1$CSCSPVHPQQAFCNADVVIRAKAVSEKEVDSGNDIYGNPIKRIQYE

IKQIKMFKGPX1KDIEFIYTAPSSAVCGVSLDVGGKKEYLIAGKAEGDGKM

HITLCDFIVPWDTLX2TTQKKSLNHRYQMGCECKITRCPMIPCYISSPDE

CLWMDWVTEKX3INGHQAKFFACIKRSDGSCAWYRGAAPPKQEFLDIED

P-$Z^2$ wherein  X1 represents  the amino acid E or D;
              X2 represents  the amino acid T or I;
              X3 represents  the amino acid N or S;
              $Z^1$ represents  —H, a substituted group or an arbitrary peptide having up to ten amino acids;
              $Z^2$ represents  —OH, $NH_2$, a substituted —$NH_2$ or an arbitrary peptide having up to ten amino acids;

and its biologically active fragments and/or amidated, acylated, sulfated, phosphorylated, glycosylated and/or polyethylene-glycol modified derivatives.

According to the invention, there are preferably employed human TMP-2 (SEQ ID NO.1) and rat TIMP-2 (SEQ ID NO.2):

CSCSPVHPQQAFCNADVVIRAKAVSEKEVDSGNDIYGNPIKRIQYEIKQIKMFKGPEKD (SEQ. ID. NO 1)
IEFIYTAPSSAVCGVSLDVGGKKEYLIAGKAEGDGKAEGDGKMHITLCDFIVPWDTLSTTQKKSLN
HRYQMGCECKITRCPMIPCYISSPDECLWMDWVTEKNINGHQAKFFACIKRSDGSCA
WYRGAAPPKQEFLDIEDP

CSCSPVHPQQAFCNADVVIPAKAVSEKEVDSGNDIYGNPIKRIQYEIKQIKMFKGPDKD (SEQ. ID. NO 2)
IEFIYTAPSSAVCGVSLDVGGKKEYLIAGKAEGDGKMHITLCDFIVPWDTLSITQKKSLN
HRYQMGCECKITRCPMIPCYISSPDECLWMDWVTEKSINGHQAKFFACIKRSDGSCA
WYRGAAPPKQEFLDIEDP

The invention also relates to the use of TIMP-2 having the amino acid sequence $Z^1$CSCSRVHPQQAFCNADVVIRAKAVSEKEVDSGNDIYGNPIKRIQYEIK
QIKMFKGPX1KDIEFIYTAPSSAVCGVSLDVGGKKEYLIAGKAEGDGKMH
ITLCDFIVPWDTLX2TTQKKSLNHRYQMGCECKITRCPMIPCYISSPDEC
LWMDWVTEKX3INGHQAKFFACIKRSDGSCAWYRGAAPP KQEFLDIED
P-$Z^2$ wherein X1 represents the amino acid E or D;
X2 represents the amino acid T or I;
X3 represents the amino acid N or S;
$Z^1$ represents —H, a substituted group or an arbitrary peptide having up to ten amino acids;
$Z^2$ represents —OH, $NH_2$, a substituted —$NH_2$ or an arbitrary peptide having up to ten amino acids;

and its biologically active fragments and/or amidated, acylated, sulfated, phosphorylated, glycosylated and/or polyethylene-glycol modified derivatives for preparing an osteoanabolic medicament.

TIMP-2 derivatives which can be used according to the invention preferably have at least 90% sequence identity with the native sequence of TIMP-2 or the mentioned modifications.

It may be advantageous to employ the TIMP-2 to be used according to the invention in combination with other growth factors and/or medicaments and in combination with medical aids, for example, in grafts.

The administration of TIMP-2 is effected, in particular, as a formulation in the form of injections, ointments, sustained release capsules and similar galenic formulations.

The invention also relates to the use of low-molecular weight substances and active compounds which have effects on bone cells comparable to those of TIMP-2 for preparing a medicament for treating diseases of the bone system, such as fractures, osteopenia and osteoporosis.

Further, the invention also relates to the use of a receptor for TIMP-2 on bone cells in connection with its related agonists and antagonists for preparing a medicament for diseases of the bone system, such as fractures, osteopenia and osteoporosis.

The TIMP-2 to be used according to the invention is employed, in particular, for preparing an osteoanabolic medicament for treating bone defects and for improving bone regeneration, especially following bone fractures or surgical intervention, and for treating degenerative and metabolic bone diseases, such as osteoporosis, osteopenia and osteomalacia, and inflammatory bone diseases, such as ostitis and osteomyelitis.

The invention also relates to a diagnostic agent for functional disorders of the bone, containing TIMP-2 having the amino acid sequence ($Z^1$-SEQ ID NO: 3-$Z^2$)
$Z^1$CSCSPVHPQQAFCNADVVIRAKAVSEKEVDSGNDIYGNPIKRIQYEIKQ
IKMFKGP
X1KDIEFIYTAPSSAVCGSLDVGGKKEYLIAGKAEGDGKMHITLCDFIVP
WDTLX2TTQKKSLNHRYQMGCECKITRCPMIPCYISSPDECLWMDWVTEK
X3INGHQAKFFACIKRSDGSCAWYRGAAPP KQEFLDIEDP-$Z^2$ wherein X1 represents the amino acid E or D;
X2 represents the amino acid T or I;
X3 represents the amino acid N or S;
$Z^1$ represents —H, a substituted group or an arbitrary peptide having up to ten amino acids;
$Z^2$ represents —OH, $NH_2$, a substituted —$NH_2$ or an arbitrary peptide having up to ten amino acids;

and its biologically active fragments and/or amidated, acylated, sulfated, phosphorylated, glycosylated and/or polyethylene-glycol modified derivatives.

The basis of the identification of TIMP-2 as an osteoanabolic peptide was the observation that there is a different ability of regeneration of bone defects depending on the age of an organism. While adult organisms are not normally capable of regenerating major bone defects by the formation of new bone tissue, a complete bony regeneration of comparable defects takes place in younger organisms.

Similar observations were also made in vitro in the examination of osteoblasts: Osteoblasts isolated from fetal organisms grow without any problems in cultures and begin to mineralize after a few days. In contrast, osteoblasts from immature and adult animals are not capable of proliferating under standard culture conditions and eventually die. If these cells, which are not viable alone, are supplemented with the supernatant of fetal osteoblasts, they proliferate and mineralize in a way similar to the fetal cells.

A clearly regenerative capability of the cell culture supernatant of fetal osteoblasts could also be shown in vivo. Thus, a skull defect which cannot heal with the formation of bone tissue without external stimulation was surgically caused to rats. However, if a peptide extract from the cell culture supernatant of fetal primary osteoblasts is administered into these defects, then a complete regeneration of the defect takes place with the formation of new bone tissue.

In order to isolate the substance which is responsible for the effects described above, a peptide extraction from the supernatant of fetal osteoblasts was performed, and the peptides obtained were subsequently examined in vitro for their osteoproliferative capabilities (see Example 3). The peptide according to the invention could be purified thereby using preparative, semipreparative and analytical RP chromatography due to its biological activity.

The biochemical characterization of the purified peptide according to the invention was effected by mass spectrometry and N-terminal sequencing. Determination of the molecular mass by electrospray mass spectrometry yielded a molecular mass of 21,715 Da. The N-terminal sequence analysis by Edman degradation resulted in the following sequence:

XSXSPVHPQQAFXNADVVIRAKAV (SEQ ID NO:4)

The substance according to the invention can be employed to induce enhanced growth and improved regeneration of bone tissue. This may be considered, in particular, after bone fractures or surgical intervention, but also in systemic bone diseases.

The invention will be illustrated in more detail by the following Examples:

EXAMPLE 1

Isolation of TIMP-2 from Cell Culture Supernatant

Cell culture supernatants were obtained from confluent cultures of primary fetal osteoblasts. Thus, the osteoblasts were first isolated from the skull caps of rat fetuses by sequential digestion with collagenase and trypsin, followed by cultivation in Eagle's minimal essential medium (MEM) with penicillin/streptomycin and 10% fetal calf serum (FCS). After confluency was reached, the cells were kept alternately with 10% FCS for 24 hours and serum-free for 24 hours. The serum-free supernatants were collected and used for further peptide isolation.

The isolation of TIMP-2 was effected by various subsequent RP-HPLC steps which served for the fractioning of the whole peptide extract. Aliquots of the fractions were tested in a bioassay. The fractions were stored at −20° C.

The different chromatographic steps for the purification of osteoproliferative TIMP-2 are shown in FIGS. 1 A–D.

1. Preparative Chromatography

The serum-free cell culture supernatants were adjusted with HCl to a pH of 2.5 and by the addition of acetonitrile to 5% acetonitrile. Subsequently, they were filtered first over a glass fiber filter (GF6, Schleicher & Schuell) and then over a membrane filter (OE G7, 4.43 µm, Schleicher & Schuell). The material thus obtained was charged onto a RP column in amounts of from 1 to 2 l with a flow rate of from 40 to 50 ml/min.

Chromatographic conditions:

| Column: | YMC Gel Basic (15–30 µm, 47 × 300 mm) |
|---|---|
| Flow: | 40 ml/min |
| Fractions: | 50 ml |
| Buffer A: | 10 mM HCl |
| Buffer B: | 80% (w/v) acetonitrile, 10 mM HCl |
| Gradient: | 5 to 75% B in 47.5 min |
|  | 75 to 100% B in 5 min. |

Subsequently, aliquots of the fractions obtained were tested in a bioassay.

2. Semipreparative Separation

Fractions 37–40, which were bioactive in the assay, were separated by means of a further RP step.

Chromatographic conditions:

| Column: | Biotek RP Silica C4 (100 A, 5 µm, 20 × 125 mm) |
|---|---|
| Flow: | 5 ml/min |
| Fraction: | 5 ml |
| Buffer A: | 0.1% TFA |
| Buffer B: | 80% (w/v) acetonitrile, 0.1% TFA |
| Gradient: | 5 to 40% B in 10 min |
|  | 40 to 100% B in 60 min. |

Aliquots of the fractions obtained were again tested in a bioassay.

3. Analytical Chromatography

The subsequent fractioning of the bioactive fractions 22 and 23 was effected by means of another RP chromatography.

Chromatographic conditions:

| Column: | YMC C18 (120 A, 5 µm, 4.6 × 250 mm) |
|---|---|
| Flow: | 0.6 ml/min |
| Fraction: | 0.6 ml |
| Buffer A: | 0.1% TFA |
| Buffer B: | 80% (w/v) acetonitrile, 0.1% TFA |
| Gradient: | 5 to 30% B in 4 min |
|  | 30 to 55% B in 50 min |
|  | 55 to 100% B in 5 min. |

Aliquots of the fractions obtained were again tested in a bioassay.

4. Analytical Chromatography

The bioactive fractions 27–29 were again separated by means of RP chromatography.

Chromatographic conditions:

| Column: | Phenomenex C5 (4.6 × 250 mm) |
|---|---|
| Flow: | 0.6 ml/min |
| Fraction: | 0.6 ml |
| Buffer A: | 0.1% TFA |
| Buffer B: | 80% (w/v) acetonitrile, 0.1% TFA |
| Gradient: | 5 to 38% B in 4 min |
|  | 38 to 58% B in 60 min |
|  | 58 to 100% B in 5 min. |

In the subsequent biotest, the peptide according to the invention could be obtained in pure form in fraction 24.

EXAMPLE 2

Biochemical Analysis of TIMP-2

1. Mass Determination

The mass determination of the native purified peptide was performed by means of an ESI mass spectrometer. A molecular mass of 27,715 Da was obtained. This is in very good agreement with the theoretical mass of the oxidized form of TIMP-2 in which all the cysteines are bridged by cystine bridges.

2. Sequence Determination

The purified native peptide was analyzed by Edman degradation on an ABI 494 sequencer using the standard program. The first 24 degradation steps yielded the following N-terminal sequence:
XSXSPVHPQQAFXNADVVIRAKAV (SEQ ID NO:4)

X are cysteine residues which cannot be detected by sequencing. Taking into account the non-detectable cysteines, the sequence obtained is exactly identical with the known sequence of TIMP-2. Minor sequences were not obtained.

3. Data Base Search

In a subsequent alignment in the data base SwissProt, the sequence was unambiguously identified as the beginning of TIMP-2. The theoretical mass of the protein of 27,713 Da is also in agreement with the measured mass of 27,715 Da. Thus, the purified peptide could be unambiguously identified as TIMP-2.

EXAMPLE 3

Determination of the Biological Peptide of TIMP-2

The isolation of TIMP-2 was effected by means of its biological activity, the proliferation of fetal rat osteoblasts being measured.

Thus, aliquots of the peptide fractions obtained were lyophilized and resuspended in serum-free medium. Subsequently, their proliferative effect on fetal osteoblasts was tested. Subsequently, fractions exhibiting a proliferative effect were subjected to another chromatographic separation. The different chromatographic steps for the purification of osteoproliferative TIMP-2 are shown in FIGS. 1 A–D.

For proliferation measurement, the primary osteoblasts were trypsinized and plated in 96 well plates in a serum-free medium in a cell density of 5000 cells per well. Subsequently, the fractions to be tested were added. After an incubation time of 48 h or 72 h, the proliferation was tested by means of two different methods. As positive controls, different concentrations of fetal calf serum and TGFβ1 were used. Cells having obtained no stimulation served as a negative control.

On the one hand, proliferation measurement was effected by means of the Wst-1 substrate. This substrate is converted by mitochondrial enzymes in metabolically active cells to a colored product, the color intensity formed being proportional to the number of cells. The color intensity is determined at a wavelength of 405 nm and a reference wavelength of above 600 nm in an ELISA reader.

On the other hand, the proliferation is measured by direct measurement of the cell number in a Coulter counter (CASY).

Figure 2:
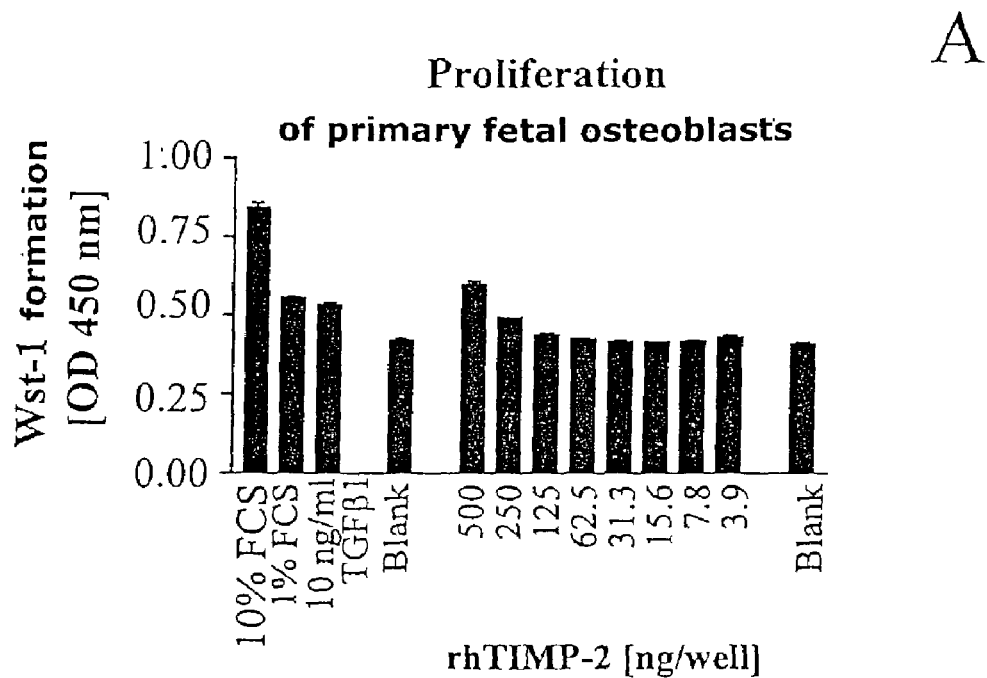
FIGS. 2A–2B show that proliferative effect of recombinant human TIMP-2 on primary fetal rat osteoblasts. B) Influence of recombinant human TIMP-2 on the average cell diameter in the mouse osteoblastic cell line MC3T3-E1.
Figure 2:
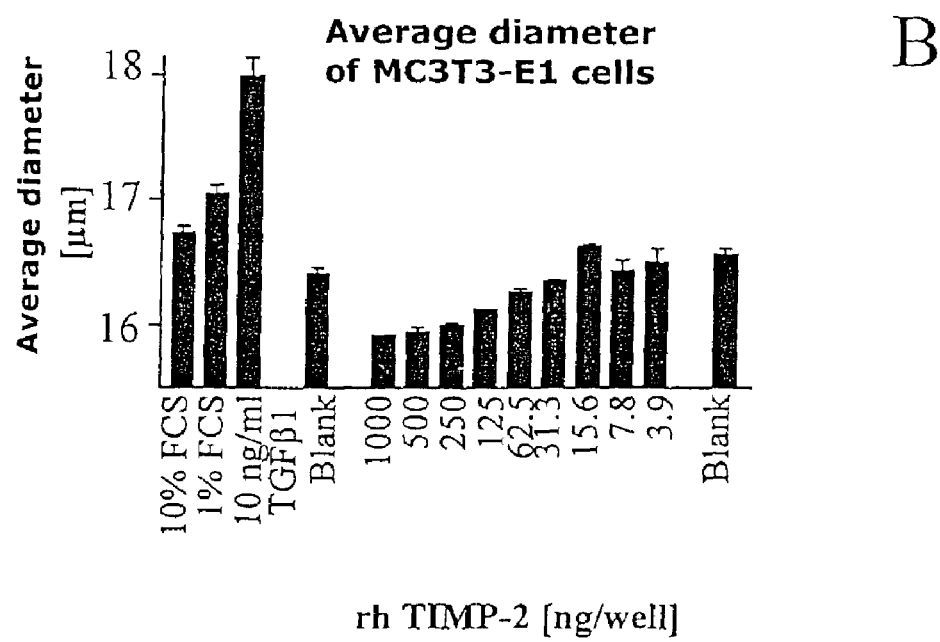

Both methods showed a dose-dependent growth-promoting effect of recombinant human TIMP-2 on osteoblasts (FIG. 2A). A significant osteoproliferative effect of TIMP-2 can be detected in these in-vitro experiments from concentrations of 100 ng/ml. In addition, human TIMP-2 causes a decrease of the average cell diameter in the mouse osteoblastic cell line MC3T3-E1 (FIG. 2B).

Significant effects of TIMP-2 can be detected in this in-vitro experiment from concentrations of 100 ng/ml. Further, a protective and proliferative effect on the mouse osteoblastic cell line MC3T3-E1 could be shown by microscopy. Since all these cells are typical bone cells, TIMP-2 can be considered an osteoanabolic factor.

The invention claimed is:

1. A method of stimulating osteoblasts after bone fracture or surgical intervention comprising administering an effective amount of a stimulating agent in combination with a graft to a patient in need thereof, wherein the stimulating agent is
   a) tissue inhibitor of metalloproteinases-2 (TIMP-2) having the amino acid sequence $Z^1$CSCSPVHPQQAFCNADVVIRAKAVSEKEVDSGNDIYGNPIKRIQYEI KQIKMFKGP(residues 1–56 of SEQ ID NO:1)

X1KDIEFIYTAPSSAVCGVSLDVGGKKEYLIAGKAEGDGKMHITLCDF

IVPWDTL (residues 58–110 of SEQ ID NO:1)

X2TTQKKSLNHRYQMGCECKITRCPMIPCYISSRDECLWMDWVTEK (residues 112–155 of SEQ ID NO:1)

X3INGHQAKFFACIKRSDGSCAWYRGAAPPKQEFLDIEDP (residues 157–194 of SEQ ID NO:1)-$Z^2$ wherein
   X1 is the amino acid E or D,
   X2 is the amino acid T or I,
   X3 is the amino acid N or S,
   $Z^1$ is hydrogen or a substituent group or an arbitrary peptide having up to ten amino acids, and
   $Z^2$ is —OH, —NH$_2$, substituted —NH$_2$ or an arbitrary peptide having up to ten amino acids,
   or
   b) the TIMP-2 of (a) modified by amidation, acylation, sulfation, phosphorylation, glycosylation, attachment of polyethylene-glycol groups, or a combination thereof, wherein the modified TIMP-2 has osteoblast stimulating activity after a bone fracture or surgical intervention,
   thereby stimulating osteoblasts.

2. The method of claim 1, wherein the stimulating agent is in a galenic formulation.

3. The method of claim 2, wherein the galenic formulation is an injection preparation, an ointment, or a sustained release capsule.

* * * * *